United States Patent
DeMattei et al.

(10) Patent No.: US 9,456,602 B2
(45) Date of Patent: Oct. 4, 2016

(54) METHOD FOR THE FORMULATION OF HAND SANITIZER

(71) Applicant: Working Bugs, LLC, East Lansing, MI (US)

(72) Inventors: Cordell DeMattei, Mt. Pleasant, MI (US); Dianne Holman, Okemos, MI (US); Peter K. Rossman, Chicago, IL (US); Thomas A. Auchtung, East Lansing, MI (US)

(73) Assignee: Working Bugs, LLC, East Lansing, MI (US)

( * ) Notice: Subject to any disclaimer, the term of this patent is extended or adjusted under 35 U.S.C. 154(b) by 83 days.

(21) Appl. No.: 14/353,365

(22) PCT Filed: Oct. 24, 2012

(86) PCT No.: PCT/US2012/061631
§ 371 (c)(1),
(2) Date: Apr. 22, 2014

(87) PCT Pub. No.: WO2013/063072
PCT Pub. Date: May 2, 2013

(65) Prior Publication Data
US 2014/0296350 A1 Oct. 2, 2014

Related U.S. Application Data

(60) Provisional application No. 61/628,077, filed on Oct. 24, 2011.

(51) Int. Cl.
| | |
|---|---|
| *A01N 25/32* | (2006.01) |
| *A01N 31/02* | (2006.01) |
| *A61K 31/045* | (2006.01) |
| *A61P 31/02* | (2006.01) |
| *A61K 8/34* | (2006.01) |
| *A61Q 17/00* | (2006.01) |
| *A61Q 19/00* | (2006.01) |
| *A61K 8/97* | (2006.01) |

(52) U.S. Cl.
CPC ............... *A01N 31/02* (2013.01); *A01N 25/32* (2013.01); *A61K 8/342* (2013.01); *A61K 8/345* (2013.01); *A61K 8/97* (2013.01); *A61K 31/045* (2013.01); *A61Q 17/005* (2013.01); *A61Q 19/00* (2013.01)

(58) Field of Classification Search
None
See application file for complete search history.

(56) References Cited

U.S. PATENT DOCUMENTS

| | | |
|---|---|---|
| 2003/0008791 A1 | 1/2003 | Chiang |
| 2003/0129180 A1* | 7/2003 | Baker ................ A43B 1/0045 424/94.61 |
| 2005/0232894 A1* | 10/2005 | Weiner et al. ............ 424/70.28 |
| 2008/0045491 A1 | 2/2008 | Fitchmun |
| 2009/0226498 A1 | 9/2009 | Flugge-Berendes et al. |

FOREIGN PATENT DOCUMENTS

WO  WO 2008067028 A2 * 6/2008 ............ A61K 8/046

OTHER PUBLICATIONS

Picheanathian, Int. J. Nursing Practice 10, 3-9 (2004).*
Dyer et al., AORN J. 68, 239-51 (1998).*
Michaels et al., Food Serv. Tech. 3, 71-80 (2003).*
Form PCT/ISA/210, International Search Report, Dated Dec. 27, 2012.

* cited by examiner

*Primary Examiner* — Theodore R West
(74) *Attorney, Agent, or Firm* — Butzel Long

(57) ABSTRACT

A hand sanitizer composition that provides effective skin sanitization and exhibits low flammability, while containing sufficient humectant for moisturization of the skin includes an alcohol selected from the group consisting of alcohol(s) containing 4 to 6 carbon atoms in an amount of from about 10% to about 60% by volume, and one or more humectants present in an amount of from about 10% to about 80% by volume.

14 Claims, No Drawings

METHOD FOR THE FORMULATION OF HAND SANITIZER

CROSS-REFERENCE TO RELATED APPLICATIONS

This application claims the benefit of PCT Application No. PCT/US2012/061631 filed Oct. 24, 2012 and U.S. Provisional Application No. 61/628,077 filed Oct. 24, 2011, which are hereby incorporated by reference in their entireties.

FIELD OF THE DISCLOSURE

This disclosure relates to antimicrobial compositions that are suitable for sanitizing skin.

BACKGROUND OF THE INVENTION

A 2010 report by Global Industry Analysts Inc. stated that the market for alcohol-based hand sanitizers is expected to grow to $402 million by 2015, citing the increased need for sanitation in rural and hard-to-service areas (Report: U.S. Hand Sanitizers Market to Exceed $402M by 2015. Occupational Health and Safety, 7 Sep. 7, 2011). With cleanliness being a need in places where water is scarce, hand sanitizers can ensure a sterile environment is preserved.

Most hand sanitizers require at least a 60% alcohol concentration to be effective, and often this alcohol is ethanol (Reynolds S A, Levy F., Walker, E S. Hand sanitizer alert. Emerg Infect Dis., 2006 March). While ethanol is effective at killing bacteria and other pathogens, other alcohols can be more effective.

A 1996 paper published in *Fundamental and Applied Toxicology* showed that longer chain alcohols, such as 1-propanol, 1-butanol, and 1-pentanol, are more effective in killing microorganisms than ethanol (McKarns, Susan C., Corwin Hansch, William S. Caldwell, Walter T. Morgan, Sarah K. Moore, and David J. Doolittle. "Correlation between Hydrophobicity of Short-Chain Aliphatic Alcohols and Their Ability to Alter Plasma Membrane Integrity; Fundamental and Applied Toxicology 36.1 (1997), pages 62-70).

One of the problems with ethanol-based hand sanitizers, however, is that to be effective the sanitizer needs a concentration of ethanol that results in making it flammable. Another problem with ethanol-based hand sanitizers is that they can be ingested to cause intoxication similar to drunkenness; many hand sanitizers have ethanol content equal to or greater than whiskey (Ahmed-Ullah, Noreen A., Despite swine flu, some take shots at hand sanitizer, Chicago Tribune, Sep. 14, 2009).

Another problem with most hand sanitizers currently on the market is that they can cause skin dryness if they are overused.

SUMMARY OF THE DISCLOSURE

Disclosed are hand sanitizer compositions containing an alcohol selected from the group consisting of alcohol(s) containing 4 to 6 carbon atoms that are adapted for application to the skin and wherein the composition is effective as a skin sanitizer exhibiting low flammability, and containing a moisturizing amount of a humectant.

In certain embodiments, the hand sanitizer composition includes one alcohol or a plurality of alcohols having from 4 to 6 carbon atoms and a single hydroxyl group, wherein the alcohol or alcohols having from 4 to 6 carbon atoms and a single hydroxyl group are present in the composition in an amount of from about 10% to about 60% by volume. Optionally, the hand sanitizer composition includes ethanol and/or propanol in a total amount up to 70% by volume. The propanol, if added, can be n-propyl alcohol, isopropyl alcohol, or a combination of n-propyl alcohol and isopropyl alcohol. The hand sanitizer composition may also optionally include water in an amount up to 20% by volume. Also included in the hand sanitizer composition is one humectant or a plurality of humectants in an amount of from about 10% to about 80% by volume.

In certain embodiments, the alcohol having 4 to 6 carbon atoms is, or the alcohols having from 4 to 6 carbon atoms are, selected from the group consisting of 1-butanol, 2-butanol, tertiary-butanol, 2 methyl butanol, 3-methyl butanol, 1-pentanol, 2-pentanol and 1-hexanol.

In certain embodiments, the alcohol having from 4 to 6 carbon atoms is, or the alcohols each having from 4 to 6 carbon atoms are, present in an amount of from about 10% to about 30% by volume, about 10% to about 20% by volume, or about 15% by volume.

In certain embodiments, the ethanol and/or propanol are present in an amount of from about 5% to about 50%, about 10% to about 40%, about 15% to about 30%, or about 20%, by volume.

In certain embodiments, water is present in an amount less than 10%, less than 5%, or less than 1%, by volume. In certain embodiments, there is no added water, although some small amount of water may be introduced with other ingredients (e.g., ethanol distilled at ambient pressure forms an azeotrope typically containing about 5% water).

In certain embodiments, the humectant is, or a plurality of humectants are, present in an amount of from about 50% to about 75%, about 60% to about 75%, or about 65%, by volume.

In certain embodiments, the humectant is, or the plurality of humectants are, selected from the group consisting of aloe vera liquid, aloe vera powder, aloe vera gel and glycerol.

DESCRIPTION OF THE INVENTION AND EXAMPLES

Disclosed is a non-flammable all-natural hand sanitizer containing at least one aliphatic alcohol having 4 to 6 carbon atoms per molecule. With the increased antimicrobial activity we can decrease the amount of total alcohol and optionally eliminate ethanol from the hand sanitizer, leaving more volume for humectants which can moisturize and protect the skin from the dryness that so often results from constant use of ethanol-based hand sanitizers.

When another alcohol that is a better antimicrobial agent than ethanol is added to a hand sanitizer, it will need less alcohol, and more of a humectant can be added that will moisturize and protect the skin from the drying effects of the alcohol.

Unless otherwise indicated, the amounts of the ingredients or components comprising the compositions of the invention are given in percentages by volume. It is recognized that the volume occupied by liquids when they are mixed can be different than the sum of the volumes that the liquids occupied before mixing. For example, when ethanol and water are mixed, the volume of the mixture is less than the sum of the volume of water and the volume of ethanol before mixing. Accordingly, while in most cases, the volume change upon mixing will be small, and often insignificant, especially in those compositions containing little or no water, the percentages by volume used herein refer to the percentages by volume before mixing.

Examples 1-4 exemplify hand sanitizers comprising about 10% to about 60% by volume of at least one alcohol from the group consisting of 1-butanol, 2-butanol, tert-butanol, 1-pentanol, 2-pentanol, and 1-hexanol (e.g., about 10% to about 30%, about 10% to about 20%, or about 15%, by volume); and ethanol, propanol, or a combination of ethanol and propanol in an amount of from 0 to about 70% by volume (e.g., about 5% to about 50%, about 10% to about 40%, about 15% to about 30%, or about 20%, by volume) as the antimicrobial agent(s). From 0 to about 20% water by weight is then added (e.g., less than 10%, less than 5%, or less than 1% by volume), and humectants are added in an amount of from about 0% to about 80% by volume of the composition (e.g., about 50% to about 75%, about 60% to about 75%, or about 65%, by volume).

Example 5 is different from the other Examples because it does not contain ethanol or propanol.

EXAMPLE 1

A 50 mL culture of the bacterium *Seratia marcescens* (*S. marcescens*) was grown, and four compounds were tested: an ethanol-based hand sanitizer currently on the market with 63% ethyl alcohol as the active ingredient, 60% isopropyl alcohol, and water as a control. 0.05 mL of the culture was exposed to one of the compounds for 15 and 60 seconds (except for the water, which was exposed for 30 seconds), and diluted by factors of powers of ten from a $10^{-1}$ dilution to a $10^{-10}$ dilution. 1 mL of each dilution was plated onto a CASO (a type of media) plate, and was incubated at 25 degrees Celsius (77 degrees Fahrenheit) for 48 hours. The colonies on the plates were then counted. The following is a table of the number of colonies on each plate (note—"Lawn" means that there were too many colonies to count individually).

TABLE 1

Growth test of *S. marcescens* bacteria when exposed to Water, 60% Isopropyl Alcohol (IPA), An ethanol-based hand sanitizer on the market (HSM), and the hand sanitizer proposed in the patent (New) containing n-butanol.

| | $10^{-1}$ | $10^{-2}$ | $10^{-3}$ | $10^{-4}$ | $10^{-5}$ | $10^{-6}$ | $10^{-7}$ | $10^{-8}$ | $10^{-9}$ | $10^{-10}$ |
|---|---|---|---|---|---|---|---|---|---|---|
| Water | Lawn | Lawn | Lawn | Lawn | Lawn | 400 | 280 | 200 | 172 | 140 |
| IPA 15 s | 0 | 0 | 0 | 0 | 0 | 0 | 0 | 0 | 0 | 0 |
| IPA 60 s | 0 | 0 | 0 | 0 | 0 | 0 | 0 | 0 | 0 | 0 |
| HSM 15 s | 0 | 0 | 0 | 0 | 0 | 0 | 0 | 0 | 0 | 0 |
| HSM 60 s | 0 | 0 | 0 | 0 | 0 | 0 | 0 | 0 | 0 | 0 |
| New 15 s | 0 | 0 | 0 | 0 | 0 | 0 | 0 | 0 | 0 | 0 |
| New 60 s | 0 | 0 | 0 | 0 | 0 | 0 | 0 | 0 | 0 | 0 |

As can be seen, the hand sanitizer proposed was just as effective in killing bacteria as 60% isopropyl alcohol and ethanol-based hand sanitizer on the market.

EXAMPLE 2

Example 2 followed the same protocol as Example 1, except *E. coli* bacteria were used instead of *S. marcescens*.

TABLE 2

Growth test of *E. coli* bacteria when exposed to Water, 60% Isopropyl Alcohol (IPA), An ethanol-based hand sanitizer on the market (HSM), and the hand sanitizer proposed in the patent (New) containing n-butanol.

| | $10^{-1}$ | $10^{-2}$ | $10^{-3}$ | $10^{-4}$ | $10^{-5}$ | $10^{-6}$ | $10^{-7}$ | $10^{-8}$ | $10^{-9}$ | $10^{-10}$ |
|---|---|---|---|---|---|---|---|---|---|---|
| Water | Lawn | Lawn | Lawn | Lawn | Lawn | Lawn | Lawn | Lawn | Lawn | >500 |
| IPA 15 s | 0 | 0 | 0 | 0 | 0 | 0 | 0 | 0 | 0 | 0 |
| IPA 60 s | 0 | 0 | 0 | 0 | 0 | 0 | 0 | 0 | 0 | 0 |
| HSM 15 s | 0 | 0 | 0 | 0 | 0 | 0 | 0 | 0 | 0 | 0 |
| HSM 60 s | 0 | 0 | 0 | 0 | 0 | 0 | 0 | 0 | 0 | 0 |
| New 15 s | 0 | 0 | 0 | 0 | 0 | 0 | 0 | 0 | 0 | 0 |
| New 60 s | 0 | 0 | 0 | 0 | 0 | 0 | 0 | 0 | 0 | 0 |

As can be seen, the hand sanitizer proposed was just as effective in killing bacteria as 60% isopropyl alcohol and an ethanol-based hand sanitizer on the market.

EXAMPLE 3

Example 3 followed the same protocol as Example 2, except for the following: A different type of growth medium was used on the plates, and 0.5 mL of culture was plated onto each plate instead of 1 mL in order to prevent flooding the plate. In this Example, 60% isopropanol, an ethanol-based hand sanitizer on the market and the hand sanitizer proposed in the patent were all exposed to bacteria for 10 seconds, than plated.

TABLE 3

Growth test of *E. coli* bacteria when exposed to Water, 60% Isopropyl Alcohol (IPA), An ethanol-based hand sanitizer on the market (HSM), and the hand sanitizer proposed in the patent (New) containing n-butanol.

|         | $10^{-1}$ | $10^{-2}$ | $10^{-3}$ | $10^{-4}$ | $10^{-5}$ | $10^{-6}$ | $10^{-7}$ | $10^{-8}$ | $10^{-9}$ | $10^{-10}$ |
|---------|-----------|-----------|-----------|-----------|-----------|-----------|-----------|-----------|-----------|------------|
| Water   | Lawn      | Lawn      | Lawn      | Lawn      | Lawn      | 88        | 58        | 57        | 33        | 95         |
| IPA 10 s| 0         | 0         | 0         | 0         | 0         | 0         | 0         | 0         | 0         | 0          |
| HSM 10 s| 0         | 0         | 0         | 0         | 0         | 0         | 0         | 0         | 0         | 0          |
| New 11 s| 0         | 0         | 0         | 0         | 0         | 0         | 0         | 0         | 0         | 0          |

As can be seen, the hand sanitizer proposed was just as effective in killing bacteria as 60% isopropyl alcohol and an ethanol-based hand sanitizer on the market.

EXAMPLE 4

In Example 4, a formulation of sanitizer with a lesser amount of the n-butanol and a greater amount of humectant (the concentration of ethanol stayed the same as in Examples 1 through 3) was tested for its antimicrobial capabilities.

Both *S. marcescens* and *E. coil* were cultured in CASO broth overnight. The cells were exposed to one of four compounds for 15 seconds: DE broth, 60% Isopropyl Alcohol (IPA), A hand sanitizer on the market with 62% ethanol as an active ingredient (HSM), and the hand sanitizer specified in the patent (WB). The samples were then diluted by factors of powers of ten from a $10^{-1}$ dilution to a $10^{-10}$ dilution. 0.1 mL of each dilution was then plated onto a CASO plate, and then incubated for 24 hours.

Note—the abbreviation "TNTC" stands for "too numerous to count". "Lawn" represents a sample that was filled with bacteria.

TABLE 4

Growth test of *E. coli* bacteria when exposed to DE Broth, 60% Isopropyl Alcohol (IPA), An ethanol-based hand sanitizer on the market (HSM), and the hand specified in Example 4 (New4) containing n-butanol for 15 seconds.

| *E. coli* | $10^{-1}$ | $10^{-2}$ | $10^{-3}$ | $10^{-4}$ | $10^{-5}$ | $10^{-6}$ | $10^{-7}$ | $10^{-8}$ | $10^{-9}$ | $10^{-10}$ |
|-----------|-----------|-----------|-----------|-----------|-----------|-----------|-----------|-----------|-----------|------------|
| DE Broth  | Tntc      | Tntc      | 667       | 118       | 17        | 5         | 7         | 5         | 15        | 57         |
| IPA       | 0         | 0         | 0         | 0         | 0         |           | Not tested|           |           |            |
| HSM       | 0         | 0         | 0         | 0         | 0         |           |           |           |           |            |
| New4      | 1         | 1         | 1         | 21        | 20        |           |           |           |           |            |

TABLE 5

Growth test of *S. marcescens* bacteria when exposed to DE Broth, 60% Isopropyl Alcohol (IPA), An ethanol-based hand sanitizer on the market (HSM), and the hand specified in Example 4 (New4) containing n-butanol for 15 seconds.

| *S. marcescens* | $10^{-1}$ | $10^{-2}$ | $10^{-3}$ | $10^{-4}$ | $10^{-5}$ | $10^{-6}$ | $10^{-7}$ | $10^{-8}$ | $10^{-9}$ | $10^{-10}$ |
|-----------------|-----------|-----------|-----------|-----------|-----------|-----------|-----------|-----------|-----------|------------|
| DE Broth        | Lawn      | tntc      | >1000     | 267       | 66        | 24        | 7         | 6         | 2         | 1          |
| IPA             | 1         | 3         | 10        | 6         | 2         |           | Not Tested|           |           |            |
| HSM             | 1         | 3         | 3         | 6         | 8         |           |           |           |           |            |
| New4            | 0         | 0         | 0         | 0         | 0         |           |           |           |           |            |

While the hand sanitizer of the present invention was not quite as effective as other compounds in killing *E. coli*, it still managed a 3-log-kill rate. The hand sanitizer described herein was also more effective than the other hand sanitizers on the market in killing *S. marcescens*.

EXAMPLE 5

For Example 5, there was no ethanol present in the hand sanitizer formulation. The formulation consisted of 45% by volume of n-butanol, 10% of the humectant, and the remainder being water. The protocol followed for Example 5 was the same as the protocol for Example 4.

TABLE 6

Growth test of E. coli bacteria when exposed to DE Broth, 60% Isopropyl Alcohol (IPA), An ethanol-based hand sanitizer on the market (HSM), and the hand specified in Example 5 (WB5)containing n-butanol for 15 seconds.

| E. coli | $10^{-1}$ | $10^{-2}$ | $10^{-3}$ | $10^{-4}$ | $10^{-5}$ | $10^{-6}$ | $10^{-7}$ | $10^{-8}$ | $10^{-9}$ | $10^{-10}$ |
|---|---|---|---|---|---|---|---|---|---|---|
| DE broth | Not tested | | | 228 | 41 | 18 | 5 | 5 | 0 | 1 |
| IPA | 0 | 0 | 0 | 0 | 0 | | Not tested | | | |
| HSM | 0 | 0 | 0 | 0 | 0 | | | | | |
| WB5 | 0 | 0 | 0 | 0 | 0 | | | | | |

TABLE 7

Growth test of S. marcescens bacteria when exposed to DE Broth, 60% Isopropyl Alcohol (IPA), An ethanol-based hand sanitizer on the market (HSM), and the hand specified in Example 5 (WB5) containing n-butanol for 15 seconds.

| S. marcescens | $10^{-1}$ | $10^{-2}$ | $10^{-3}$ | $10^{-4}$ | $10^{-5}$ | $10^{-6}$ | $10^{-7}$ | $10^{-8}$ | $10^{-9}$ | $10^{-10}$ |
|---|---|---|---|---|---|---|---|---|---|---|
| DE broth | Not tested | | | 555 | 111 | 70 | 38 | 24 | 6 | 2 |
| IPA | 0 | 0 | 0 | 0 | 0 | | Not Tested | | | |
| HSM | 0 | 0 | 0 | 0 | 0 | | | | | |
| WB5 | 0 | 0 | 0 | 0 | 0 | | | | | |

As the data shows, the hand sanitizer disclosed herein was just as effective at killing bacteria as other hand sanitizers and methods.

In Examples 1-3, the composition was 20% n-butanol, 20% ethanol, 60% water mixed with dissolved aloe vera powder (39 parts water to 1 part aloe vera powder by mass).

In Example 4, the composition was 15% n-butanol, 20% ethanol, 65% water mixed with dissolved aloe vera powder (39 parts water to 1 part aloe vera powder by mass).

In Example 5, the composition was 45% n-butanol, 45% water and 10% glycerol.

Similar results can be achieved with other alcohols containing 4 to 6 carbon atoms.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

What is claimed is:

1. A hand sanitizer composition consisting of:
   from 10% to 30% by volume of at least one alcohol having from 4 to 6 carbon atoms and a single hydroxyl group;
   optionally, ethanol and/or propanol in a total amount of from about 10% to about 40% by volume; and
   the balance being water and from about 50% to about 75% by volume of at least one natural humectant.

2. The composition of claim 1, in which at least one alcohol having from 4 to 6 carbon atoms is selected from the group consisting of 1-butanol, 2-butanol, tertiary-butanol, 2-methyl butanol, 3-methyl butanol, 1-pentanol, 2-pentanol and 1-hexanol.

3. The composition of claim 1, wherein the alcohol having from 4 to 6 carbon atoms is, or the alcohols each having from 4 to 6 carbon atoms are, present in an amount of from about 10% to about 20% by volume.

4. The composition of claim 1, wherein the alcohol having from 4 to 6 carbon atoms is, or the alcohols each having from 4 to 6 carbon atoms are, present in an amount of about 15% by volume.

5. The composition of claim 1, wherein the ethanol and/or the propanol are present in an amount of from about 15% to about 30% by volume.

6. The composition of claim 1, wherein the ethanol and/or the propanol are present in an amount of about 20% by volume.

7. The composition of claim 1, wherein water is present in an amount less than 10%.

8. The composition of claim 1, wherein water is present in an amount less than 5%.

9. The composition of claim 1, wherein water is present in an amount less than 1%.

10. The composition of claim 1, wherein the humectant is, or plurality of the humectants are, present in an amount of from about 60% to about 75% by volume.

11. The composition of claim 1, wherein the humectant is, or plurality of humectants are, present in an amount of about 65% by volume.

12. The composition of claim 1, wherein the humectant is, or the plurality of humectants are, selected from the group consisting of aloe vera liquid, aloe vera powder, aloe vera gel and glycerol.

13. The composition of claim 1, wherein the composition comprises 20% 1-butanol by volume, 20% ethanol by volume, and 60% by volume of a mixture of aloe vera powder dissolved in water, wherein the mixture comprises 39 parts by mass of water to 1 part by mass of aloe vera powder.

14. The composition of claim 1, wherein the composition comprises about 15% 1-butanol by volume, about 20% ethanol by volume, and about 65% by volume of a mixture of aloe vera powder dissolved in water, wherein the mixture comprises 39 parts by mass of water to 1 part by mass of aloe vera powder.

* * * * *